(12) United States Patent
Lee et al.

(10) Patent No.: US 8,232,442 B2
(45) Date of Patent: Jul. 31, 2012

(54) SEPARATION METHOD OF AROMATIC COMPOUNDS COMPRISING SIMULATED MOVING BED XYLENE MIXTURE PRE—TREATMENT PROCESS AND ADDITIONAL XYLENE ISOMERIZATION PROCESS

(75) Inventors: Jin-Suk Lee, Seoul (KR); Hyun-Chul Kim, Seosan-si (KR)

(73) Assignee: Samsung Total Petrochemicals Co., Ltd., Daesan (KR)

( * ) Notice: Subject to any disclaimer, the term of this patent is extended or adjusted under 35 U.S.C. 154(b) by 312 days.

(21) Appl. No.: 12/532,728

(22) PCT Filed: Oct. 31, 2007

(86) PCT No.: PCT/KR2007/005468
§ 371 (c)(1),
(2), (4) Date: Dec. 29, 2009

(87) PCT Pub. No.: WO2008/133383
PCT Pub. Date: Nov. 6, 2008

(65) Prior Publication Data
US 2010/0105971 A1   Apr. 29, 2010

(30) Foreign Application Priority Data
Apr. 27, 2007   (KR) .................. 10-2007-0041570

(51) Int. Cl.
*C07C 7/14*   (2006.01)
(52) U.S. Cl. ........ 585/814; 585/812; 585/813; 585/815; 585/479
(58) Field of Classification Search .................. None
See application file for complete search history.

(56) References Cited

U.S. PATENT DOCUMENTS

| | | |
|---|---|---|
| 5,284,992 A | 2/1994 | Hotier et al. |
| 5,329,060 A | 7/1994 | Swift |
| 5,401,476 A | 3/1995 | Hotier et al. |
| 5,629,467 A | 5/1997 | Hotier et al. |
| 5,866,740 A | 2/1999 | Mikitenko et al. |
| 5,922,924 A | 7/1999 | Hotier et al. |
| 5,948,950 A | 9/1999 | Hotier et al. |
| 6,004,452 A | 12/1999 | Ash et al. |
| 6,060,634 A * | 5/2000 | Mikitenko et al. ............ 585/814 |
| 6,063,978 A | 5/2000 | Hotier et al. |
| 6,281,406 B1 | 8/2001 | Cain |
| 6,342,649 B1 | 1/2002 | Winter et al. |
| 6,376,734 B1 | 4/2002 | Magne-Drisch et al. |
| 6,399,846 B1 * | 6/2002 | MacPherson et al. ........ 585/814 |
| 6,774,273 B2 | 8/2004 | Xie et al. |
| 6,841,714 B2 | 1/2005 | Leflaive et al. |

OTHER PUBLICATIONS

International search report dated Jan. 22, 2008 in corresponding PCT/KR2007/005468.

* cited by examiner

*Primary Examiner* — Tam M Nguyen
(74) *Attorney, Agent, or Firm* — Young & Thompson

(57) ABSTRACT

Disclosed is a method for separating aromatic compounds using a simulated moving bed adsorptive chromatography and a crystallization process, comprising a sulfolan process that is a non-aromatic compound removing process, a benzene/toluene fractionation process, an aromatic compound fractionation process, a selective toluene disproportionation process, a transalkylation process, a crystallization process for para-xylene separation, a simulated moving bed para-xylene separation process and a xylene isomerization process, wherein the method is characterized by further comprising a simulated moving bed xylene mixture pre-treatment process and an additional xylene isomerization process. The separation method of aromatic compounds according to the present invention can make significant improvement in para-xylene and benzene production in the overall process, as compared to the conventional aromatic compound separation process.

18 Claims, 4 Drawing Sheets

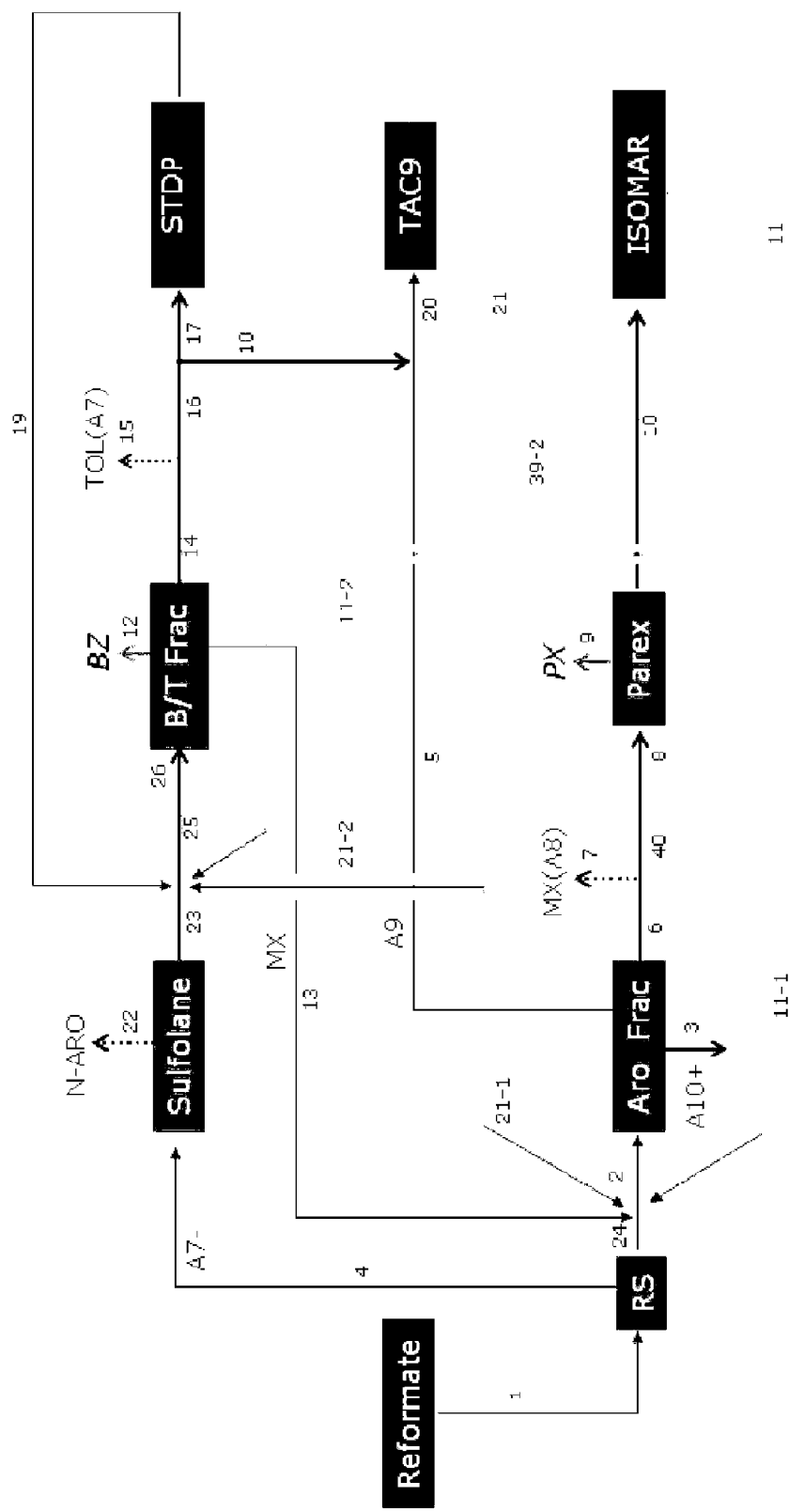
[Fig. 1]

[Fig. 2]
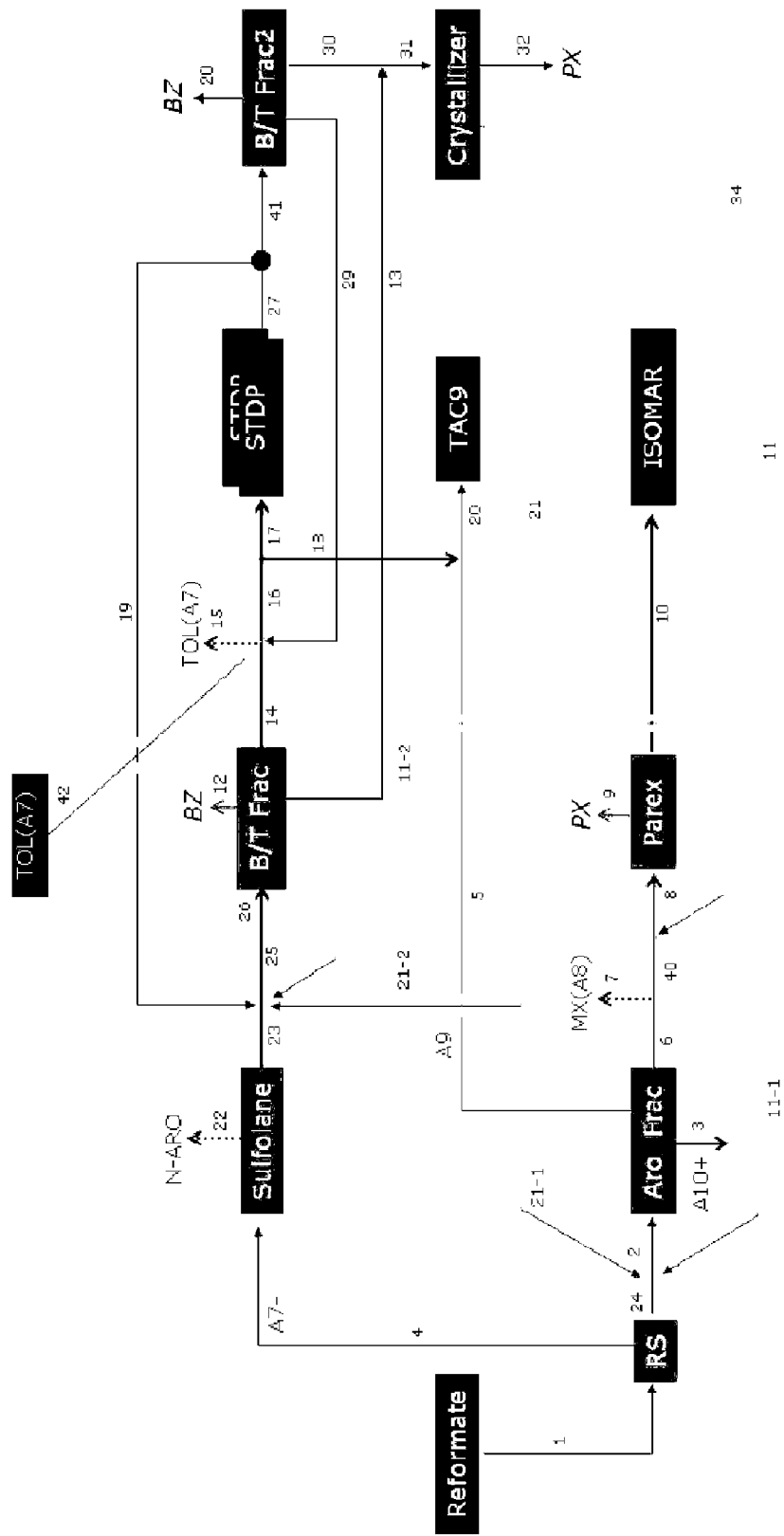

[Fig. 3]
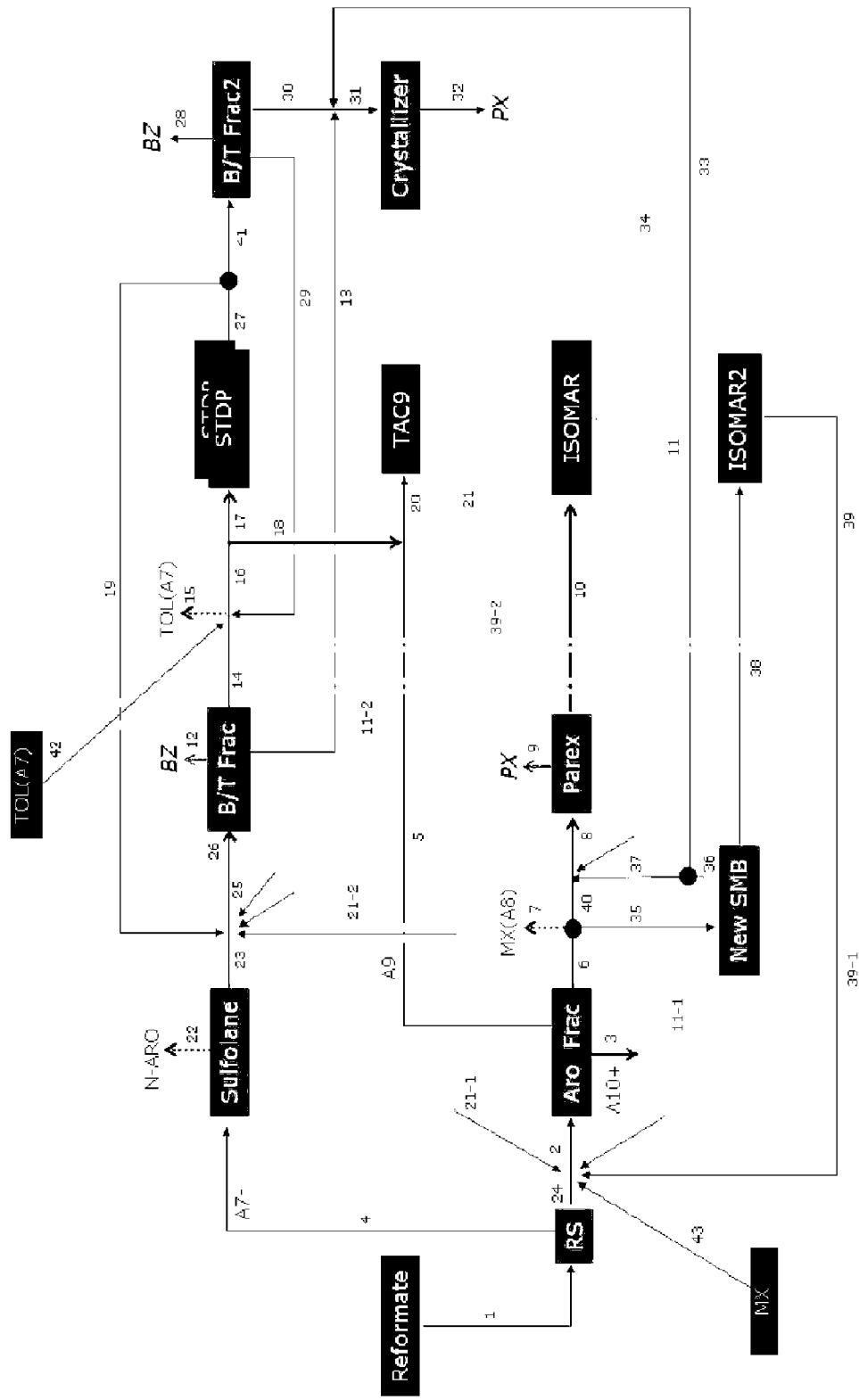

[Fig. 4]
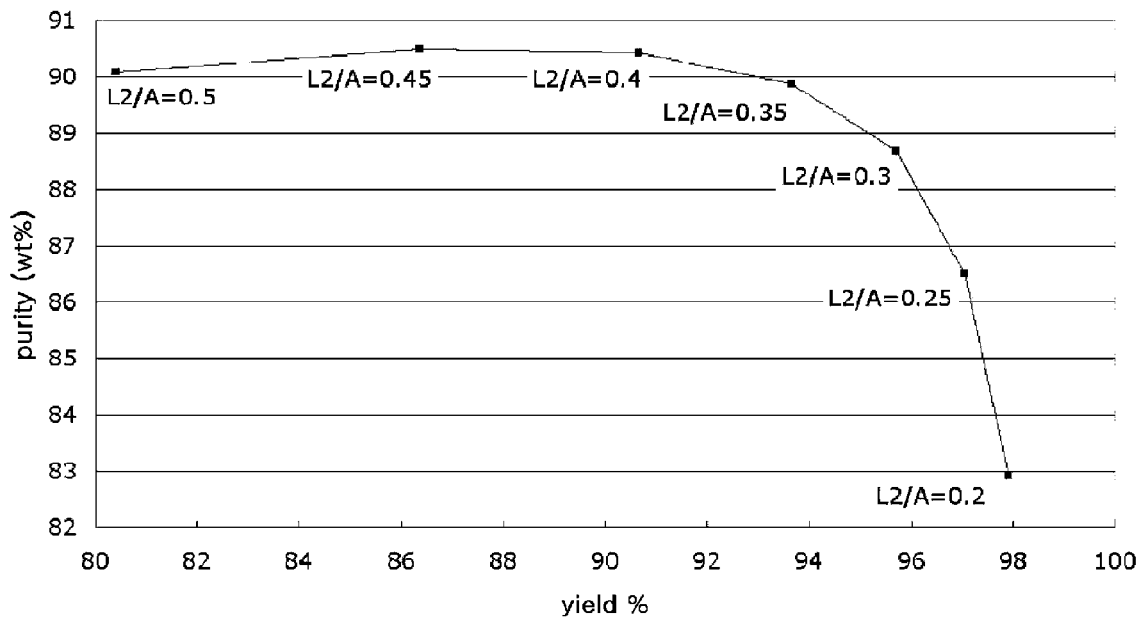
[Fig. 5]
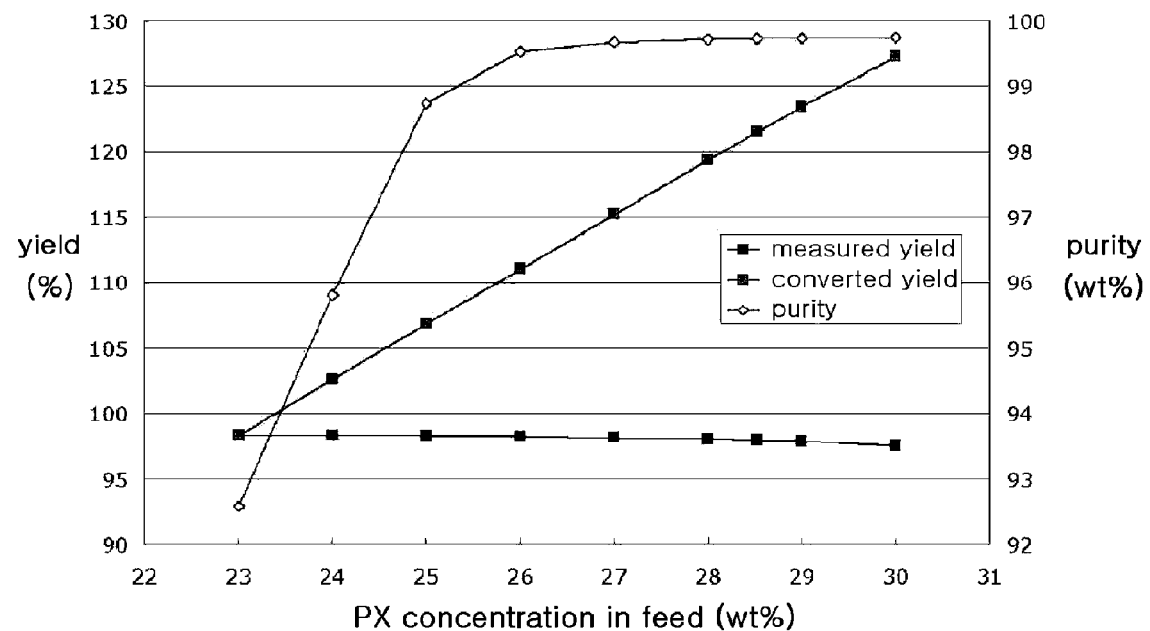

SEPARATION METHOD OF AROMATIC COMPOUNDS COMPRISING SIMULATED MOVING BED XYLENE MIXTURE PRE—TREATMENT PROCESS AND ADDITIONAL XYLENE ISOMERIZATION PROCESS

TECHNICAL FIELD

The present invention relates to a method for separating aromatic compounds using a simulated moving bed adsorptive chromatography and a crystallization process, comprising a sulfolan process that is a non-aromatic compound removing process, a benzene/toluene fractionation process, an aromatic compound fractionation process, a selective toluene disproportionation process, a transalkylation process, a crystallization process for para-xylene separation, a simulated moving bed para-xylene separation process and a xylene isomerization process, wherein the method is characterized by further comprising a simulated moving bed xylene mixture pre-treatment process and an additional xylene isomerization process.

BACKGROUND ART

A process of separating aromatic compounds is to obtain para-xylene and benzene as main final products by processing a naphtha feedstock in a petrochemical plant. To obtain para-xylene, one of important products among aromatic compounds, a process of separating it from a xylene mixture has been commonly used. As examples of such process, there are processes using simulated moving bed adsorptive chromatography and crystallization caused by freezing point difference in each component, or a hybrid process which uses both processes together by connecting them serially, and the like.

In a process of separating aromatic compounds using a conventional simulated moving bed adsorptive chromatography as shown in FIG. 1, the simulated moving bed para-xylene separation process is only used as a process for separating para-xylene. Such process has some problems that there is limitation on increasing reformate production by inputting additional naphtha, due to the limited capacity of a simulated moving bed para-xylene separation process.

For complementing the problem, by noticing that para-xylene concentration in a xylene mixture from the product resulted from a selective toluene disproportionation process (STDP) nearly reaches to approximately 90 wt %, a hybrid process in which a crystallizer is attached to the selective toluene disproportionation process as represented in FIG. 2 have been developed. Owing to such system of dividing a para-xylene separation process, it became possible to increase reformate by additional naphtha input, or to improve para-xylene productivity by additional toluene input.

DISCLOSURE OF INVENTION

Technical Problem

Such process still has defect of a simulated moving bed para-xylene separation process disclosed in FIG. 1, i.e. still having a problem that it should discharge the excess xylene mixture which could not be processed in the simulated moving bed para-xylene separation process, since a mother liquor generated from the separation process of a crystallizer is again circulated to the simulated moving bed para-xylene separation process. Therefore, it has been in need for improving productivity in terms of para-xylene production.

Technical Solution

The present invention has been developed to resolve the conventional technical problems in prior arts. The object of the present invention is to provide a method for separating aromatic compounds using a simulated bed adsorptive chromatography and a crystallization process, which can increase para-xylene concentration, hence being able to separate para-xylene in efficient way and effectively converting the excess xylene mixture into para-xylene by pretreating a xylene mixture through a simulated moving bed xylene mixture pre-treatment process and an additional xylene isomerization process; and can significantly improve the overall productivity of para-xylene and toluene by inputting a separate toluene mixture as well as a xylene mixture.

In order to achieve the forgoing purposes, the method for separating aromatic compounds according to the present invention, which uses a simulated moving bed adsorptive chromatography and a crystallization process, comprising a sulfolan process that is a non-aromatic compound removing process, a benzene/toluene fractionation process, an aromatic compound fractionation process, a selective toluene disproportionation process, a transalkylation process, a crystallization process for para-xylene separation, a simulated moving bed para-xylene separation process and a xylene isomerization process, is characterized by further comprising a simulated moving bed xylene mixture pre-treatment process and an additional xylene isomerization process.

The xylene mixture pre-treatment process and the additional xylene isomerization process preferably comprise the following steps of:

(1) inputting a part of a xylene mixture that is to be inputted to the simulated moving bed para-xylene separation process, to the simulated moving bed xylene mixture pre-treatment process;

(2) inputting a xylene mixture containing 80% by weight or more para-xylene in the resulted product obtained from said simulated moving bed xylene mixture pre-treatment process, to the crystallization process for para-xylene separation, and the remaining portion of the xylene mixture is inputted to the additional xylene isomerization process;

(3) re-inputting the resulted product obtained from the additional xylene isomerization process to the aromatic compound fractionation process.

In the step (1), the amount of a xylene mixture to be inputted to a simulated moving bed xylene mixture pre-treatment process is not specifically limited, and it may be suitably adjusted depending on the system conditions, however, preferably being 50-200 tons/hour.

In the step (2), a part of the xylene mixture containing 80% by weight or more para-xylene to be inputted to the crystallization process for para-xylene separation may be input to the simulated moving bed para-xylene separation process. The amount to be inputted is not specifically limited, and it may be suitably adjusted depending on the system conditions, however, preferably being 10~60 tons/hour.

In the step (3), a part of the product obtained from an additional xylene isomerization process, which is to be inputted to an aromatic compound fractionation process, may be inputted to a benzene/toluene fractionation process. The amount thereof to be inputted is not specifically limited, and it may be suitably adjusted depending on the system conditions, however, preferably being 1~10 tons/hour.

In the method for separating aromatic compounds, overall productivity of para-xylene may be improved, by additionally inputting toluene to a selective disproportionation process. Further, in the method for separating aromatic compounds, a xylene mixture can be additionally inputted to said aromatic compound fractionation process so as to improve overall productivity of para-xylene. Each amount of separate toluene and the separate xylene mixture to be inputted is not specifically limited, and it may be suitably adjusted depending on the system conditions, however preferably being 0~150 tons/hour and 0~60 tons/hour, respectively.

Hereinafter, the method for separating aromatic compounds of the present invention is further described in detail by referencing FIG. 3.

Reformate that is a mixture of aromatic compound feedstocks inputted from a reformer into a splitter (RS) is separated into a mixture containing aromatic compounds having 6 carbon atoms such as benzene and aromatic compounds having 7 carbon atoms such as toluene, and a mixture containing relatively heavy aromatic compounds such as xylene having 8 carbon atoms. The former is inputted to a sulfolan process (Sulfolane) that is to remove non-aromatics, and a benzene/toluene fractionation process (B/T Frac) through line (4), and the latter is inputted to an aromatic compound fractionation process (Aro Frac) through line (24).

In the benzene/toluene fractionation process, a mixture of benzene and toluene is separated to benzene and toluene, respectively, wherein benzene is discharged through line (12), and toluene is inputted to a selective toluene disproportionation process (STDP) and transalkylation process (TAC9) through line (14). The mixture resulted from a selective disproportionation reaction in the selective toluene disproportionation process contains benzene (A6), toluene (A7), xylene (A8), trimethylbenzene (A9) and the like, and particularly it contains para-xylene at the amount of about 85~95% by weight. The mixture is re-inputted to the benzene-toluene fractionation process through line (19), and a certain portion of the other is inputted to an additional benzene/toluene fractionation process (B/T Frac2) through line (41). The mixture inputted to the additional benzene/toluene fractionation process is separated into benzene, toluene and a xylene mixture, respectively, wherein benzene is discharged through line (28); toluene is re-inputted to the selective toluene disproportionation process through line (29); and the xylene mixture is directed to a crystallization process for para-xylene separation (Crystallizer) through line (30) and line (31). The xylene mixture inputted to the crystallization process for para-xylene separation is separated to para-xylene and other xylene mixture, wherein the former is discharged through line (32) and the latter is discharged through line (34) and inputted to a simulated moving bed para-xylene separation process (Parex). In the mixture inputted to the benzene/toluene fractionation process, xylene having 8 carbon atoms and trimethylbenzene that is heavier than xylene are separated from the relatively light components, discharged through line (13), and input to the crystallization process for para-xylene separation through line (31).

In the aromatic compound fractionation process, aromatic compounds having 10 or more carbon atoms are discharged through line (3), and a xylene mixture is discharged through line (6) and input to the simulated moving bed para-xylene separation process (Parex). A part of the xylene mixture is inputted to a simulated moving bed xylene mixture pre-treatment process (New SMB). The xylene mixture inputted to the simulated moving bed xylene mixture pre-treatment process through line (35) is separated to a xylene mixture at high concentration having 80 wt % or more of para-xylene, and the residual xylene mixture. A part of the former is directed to the crystallization process for para-xylene separation through line (33) and para-xylene among the resulted product therefrom is discharged through line (32), the other of the former is inputted to the simulated moving bed para-xylene separation process through line (36) and line (37). The latter is inputted to an additional xylene isomerization process (ISOMAR2) through line (38). The products resulted from the additional xylene isomerization process is transferred via line (39) to desired processes; a portion is re-inputted to the aromatic compound fractionation process through line (39-1), and the other portion is inputted to a benzene/toluene fractionation process through line (39-2).

The xylene mixture inputted to the simulated moving bed para-xylene separation process through line (8) is separated to para-xylene and the residual xylene mixture. The former is discharged through line (9), and the latter is inputted to a xylene isomerization process (ISOMAR) through line (10). The product resulted from the xylene isomerization process is re-inputted to the aromatic compound fractionation process through line (11).

The aromatic compounds having 9 carbon atoms (A9) discharged from the aromatic compound fractionation process are inputted to a transalkylation process (TAC9) through line (20). Aromatic compounds having 9 carbon atoms inputted to the transalkylation process undergoes transalkylation with toluene inputted through line (18) from the benzene/toluene separation process, thus producing a resulted mixture containing para-xylene. The resulted mixture is re-inputted to the aromatic compound fractionation process through line (21).

Additional toluene is inputted to the line (14) via line (42), and the additional toluene mixture is inputted to the line (2) via line (43).

BRIEF DESCRIPTION OF THE DRAWINGS

FIG. 1 is a schematic view of a conventional process of separating aromatic compounds using simulated moving bed adsorptive chromatography.

FIG. 2 is a schematic view of a process of separating aromatic compounds using a hybrid process comprising a conventional simulated moving bed adsorptive chromatography and crystallization.

FIG. 3 is a schematic view of a process of separating aromatic compounds comprising a xylene mixture pre-treatment process and an additional xylene isomerization process according to the present invention.

FIG. 4 is a graph showing the operation potential of a simulated moving bed xylene mixture pre-treatment process in 8 beds, which can maintain the concentration of para-xylene in an extract at 80% by weight or more by suitably adjusting the operation conditions.

FIG. 5 is a graph showing the change of productivity represented as a change of converted yield as a function of a change in para-xylene concentration in a xylene mixture inputted into a simulated moving bed para-xylene separation process which is to separate para-xyelene. The converted yield may have a value of more than 100% because it was calculated on the base of 23% of para-xylene concentration in a xylene mixture.

DEFINITIONS

Sulfolane: a process of benzene/toluene fractionation and a process of removing non-aromatic compounds Parex: a simulated moving bed para-xylene separation process
ISOMAR: a xylene isomerization process
ISOMAR2: an additional xylene isomerization process
STDP: a selective toluene disproportionation process
TAC9: a transalkylation process of aromatic compounds having 9 carbon atoms
B/T Frac: a benzene/toluene fractionation process
B/T Frac2: an additional benzene/toluene fractionation process
Aro Frac: an aromatic compound fractionation process
New SMB: a simulated moving bed xylene mixture pre-treatment process
Crystallizer: a crystallization process for para-xylene separation
A6: aromatic compounds having 6 carbon atoms
A7: aromatic compounds having 7 carbon atoms
A8: aromatic compounds having 8 carbon atoms
A9: aromatic compounds having 9 carbon atoms
A10+: aromatic compounds having 10 or more carbon atoms
BZ: benzene
PX: para-xylene
MX: xylene mixture
TOL: toluene Mode for the Invention The present invention will be further specified through the following examples, which are described with only illustrative purpose, and by no means intended to limiting or restricting the scope of the present invention.

EXAMPLES OF THE INVENTION

Example

The continuous production of para-xylene and benzene from naphtha using an aromatic compound separation process represented in FIG. 3 was carried out.

Comparative Example 1

The production as in the Example was computer-simulated in the same way, except that an aromatic compound separation process represented in FIG. 1 was used.

Comparative Example 2

The production as in the Example was computer-simulated in the same way, except that an aromatic compound separation process represented in FIG. 2 was used.

The feed amount to the simulated moving bed para-xylene process in the above Example was limited to 262 tons/hour or less that is an identical level with those of Comparative examples 1 and 2, and the feed amount to the simulated moving bed xylene mixture pre-treatment process was limited to 150 tons/hour or less. Such limitation is only to illustrate the present invention, however, by no means limiting or restricting the scope of the present invention sought to be protected.

Table 1 shows the results of the Example wherein a separate toluene was additionally inputted, and all of the product resulted from a simulated moving bed xylene mixture pre-treatment process was inputted to a simulated moving bed para-xylene separation process, and the Comparative examples 1 and 2: the amount of naphtha feedstock consumed during the production period; the intermediately produced amount of reformate; each amount of para-xylene and benzene produced; and the para-xylene concentration in the feed to the simulated moving bed para-xylene separation process.

TABLE 1

| | Example | Com. Example 1 | Com. Example 2 |
|---|---|---|---|
| Naphtha feedstock consumption (ton/hour) | 353.0 | 353.0 | 353.0 |
| Reformate production (ton/hour) | 176.0 | 176.0 | 176.0 |
| Toluene input (ton/hour) | 93.0 | 0.0 | 70.0 |
| Xylene mixture input (ton/hour) | 0.0 | 0.0 | 0.0 |
| Para-xylene production (ton/hour) | 129.4 | 70.6 | 97.7 |
| Benzene production (ton/hour) | 95.9 | 49.3 | 82.0 |
| Excess xylene mixture (ton/hour) | 0.0 | 7.0 | 22.6 |
| Excess toluene (ton/hour) | 0.0 | 5.3 | 0.0 |
| Feed rate to Parex process (ton/hour) | 261.7 | 261.5 | 261.6 |
| Para-xylene concentration in the feed to Parex process | 33.2 wt % | 27.8 wt % | 23.6 wt % |

Reviewing the results shown in Table 1, the para-xylene concentration in the feed to the simulated moving bed para-xylene separation process in the Example according to the present invention was significantly improved as compared to the Comparative example 2, and each amount of para-xylene and benzene produced from the process during the same period was increased by 31.7 tons/hour and 13.9 tons/hour, respectively, as compared to the Comparative example 2. When it is calculated as production in one year, it can be found that production increment of 278,000 tons and 122,000 tons may be obtained, respectively.

Table 2 shows the results of the Example wherein a separate toluene was additionally inputted, and 30% of the product resulted from the simulated moving bed xylene mixture pre-treatment process was inputted to a simulated moving bed para-xylene separation process and 70% was inputted to a crystallizer, and the Comparative examples 1 and 2: the amount of naphtha feedstock consumed during the production period; the intermediately produced amount of reformate; each amount of para-xylene and benzene produced; and the para-xylene concentration in the feed to the simulated moving bed para-xylene separation process.

TABLE 2

| | Example | Com. Example 1 | Com. Example 2 |
|---|---|---|---|
| Naphtha feedstock consumption (ton/hour) | 353.0 | 353.0 | 353.0 |
| Reformate production (ton/hour) | 176.0 | 176.0 | 176.0 |
| Toluene input (ton/hour) | 116.0 | 0.0 | 70.0 |
| Xylene mixture input (ton/hour) | 0.0 | 0.0 | 0.0 |
| Para-xylene production (ton/hour) | 141.8 | 70.6 | 97.7 |
| Benzene production (ton/hour) | 106.4 | 49.3 | 82.0 |
| Excess xylene mixture (ton/hour) | 0.0 | 7.0 | 22.6 |
| Excess toluene (ton/hour) | 0.0 | 5.3 | 0.0 |
| Feed rate to Parex process (ton/hour) | 261.7 | 261.5 | 261.6 |
| Para-xylene concentration in the feed to Parex process | 27.2 wt % | 27.8 wt % | 23.6 wt % |

Reviewing the results shown in Table 2, the para-xylene concentration in the feed to the simulated moving bed para-xylene separation process in the Example according to the present invention was significantly improved as compared to the Comparative example 2, and each amount of para-xylene and benzene produced from the process during the same period was increased by 44.1 tons/hour and 24.4 tons/hour, respectively, as compared to the Comparative example 2.

When it is calculated as production in one year, it can be found that production increment of 386,000 tons and 214,000 tons may be obtained, respectively.

Table 3 shows the results of the Example wherein a separate toluene was additionally inputted, and all of the product resulted from the simulated moving bed xylene mixture pre-treatment process was inputted to a crystallizer, and the Comparative examples 1 and 2: the amount of naphtha feedstock consumed during the production period; the intermediately produced amount of reformate; each amount of para-xylene and benzene produced; and the para-xylene concentration in the feed to the simulated moving bed para-xylene separation process.

TABLE 3

|  | Example | Com. Example 1 | Com. Example 2 |
| --- | --- | --- | --- |
| Naphtha feedstock consumption (ton/hour) | 353.0 | 353.0 | 353.0 |
| Reformate production (ton/hour) | 176.0 | 176.0 | 176.0 |
| Toluene input (ton/hour) | 125.0 | 0.0 | 70.0 |
| Xylene mixture input (ton/hour) | 0.0 | 0.0 | 0.0 |
| Para-xylene production (ton/hour) | 146.7 | 70.6 | 97.7 |
| Benzene production (ton/hour) | 110.5 | 49.3 | 82.0 |
| Excess xylene mixture (ton/hour) | 0.0 | 7.0 | 22.6 |
| Excess toluene (ton/hour) | 0.0 | 5.3 | 0.0 |
| Feed rate to Parex process (ton/hour) | 261.1 | 261.5 | 261.6 |
| Para-xylene concentration in the feed to Parex process | 24.7 wt % | 27.8 wt % | 23.6 wt % |

Reviewing the results shown in Table 3, the para-xylene concentration in the feed to the simulated moving bed para-xylene separation process in the Example according to the present invention was improved as compared to the Comparative example 2, and each amount of para-xylene and benzene produced from the process during the same period was increased by 49 tons/hour and 28.5 tons/hour, respectively, as compared to the Comparative example 2. When it is calculated as production in one year, it can be found that production increment of 429,000 tons and 250,000 tons may be obtained, respectively.

Table 4 shows the results of the Example wherein a separate xylene, instead of toluene, was inputted, and all of the product resulted from the simulated moving bed xylene mixture pre-treatment process was inputted to a crystallizer, and the Comparative examples 1 and 2: the amount of naphtha feedstock consumed during the production period; the intermediately produced amount of reformate; each amount of para-xylene and benzene produced; and the para-xylene concentration in the feed to the simulated moving bed para-xylene separation process.

TABLE 4

|  | Example | Com. Example 1 | Com. Example 2 |
| --- | --- | --- | --- |
| Naphtha feedstock consumption (ton/hour) | 353.0 | 353.0 | 353.0 |
| Reformate production (ton/hour) | 176.0 | 176.0 | 176.0 |
| Toluene input (ton/hour) | 0.0 | 0.0 | 70.0 |
| Xylene mixture input (ton/hour) | 34.0 | 0.0 | 0.0 |
| Para-xylene production (ton/hour) | 109.1 | 70.6 | 97.7 |
| Benzene production (ton/hour) | 57.1 | 49.3 | 82.0 |
| Excess xylene mixture (ton/hour) | 0.0 | 7.0 | 22.6 |
| Excess toluene (ton/hour) | 0.0 | 5.3 | 0.0 |
| Feed rate to Parex process (ton/hour) | 260.1 | 261.5 | 261.6 |
| Para-xylene concentration in the feed to Parex process | 24.9 wt % | 27.8 wt % | 23.6 wt % |

Reviewing the results shown in Table 4, the para-xylene concentration in the feed to the simulated moving bed para-xylene separation process in the Example according to the present invention was improved as compared to the Comparative example 2, and the amount of para-xylene produced from the process during the same period was increased by 11.4 tons/hour, as compared to the Comparative example 2. When it is calculated as production in one year, it can be found that production increment of 100,000 tons may be obtained.

Table 5 shows the results of the Example wherein a separate toluene and a separate xylene mixture were inputted, and all of the product resulted from the simulated moving bed xylene mixture pre-treatment process was inputted to a crystallizer, and the Comparative examples 1 and 2: the amount of naphtha feedstock consumed during the production period; the intermediately produced amount of reformate; each amount of para-xylene and benzene produced; and the para-xylene concentration in the feed to the simulated moving bed para-xylene separation process.

TABLE 5

|  | Example | Com. Example 1 | Com. Example 2 |
| --- | --- | --- | --- |
| Naphtha feedstock consumption (ton/hour) | 353.0 | 353.0 | 353.0 |
| Reformate production (ton/hour) | 176.0 | 176.0 | 176.0 |
| Toluene input (ton/hour) | 50.0 | 0.0 | 70.0 |
| Xylene mixture input (ton/hour) | 20.0 | 0.0 | 0.0 |
| Para-xylene production (ton/hour) | 123.8 | 70.6 | 97.7 |
| Benzene production (ton/hour) | 78.6 | 49.3 | 82.0 |
| Excess xylene mixture (ton/hour) | 0.0 | 7.0 | 22.6 |
| Excess toluene (ton/hour) | 0.0 | 5.3 | 0.0 |
| Feed rate to Parex process (ton/hour) | 261.0 | 261.5 | 261.6 |
| Para-xylene concentration in the feed to Parex process | 24.8 wt % | 27.8 wt % | 23.6 wt % |

Reviewing the results shown in Table 5, the para-xylene concentration in the feed to the simulated moving bed para-xylene separation process in the Example according to the present invention was improved as compared to the Comparative example 2, and the amount of para-xylene produced from the process during the same period was increased by 26.1 tons/hour, as compared to the Comparative example 2. When it is calculated as production in one year, it can be found that production increment of 229,000 tons may be obtained.

Table 6 shows the results of the Example wherein a separate toluene was inputted, the feed amount of reformate was increased, and all of the product resulted from the simulated moving bed xylene mixture pre-treatment process was inputted to a crystallizer, and the Comparative examples 1 and 2: the amount of naphtha feedstock consumed during the production period; the intermediately produced amount of reformate; each amount of para-xylene and benzene produced; and the para-xylene concentration in the feed to the simulated moving bed para-xylene separation process.

TABLE 6

|  | Example | Com. Example 1 | Com. Example 2 |
| --- | --- | --- | --- |
| Naphtha feedstock consumption (ton/hour) | 421.0 | 353.0 | 353.0 |
| Reformate production (ton/hour) | 210.0 | 176.0 | 176.0 |
| Toluene input (ton/hour) | 70.0 | 0.0 | 70.0 |
| Xylene mixture input (ton/hour) | 0.0 | 0.0 | 0.0 |
| Para-xylene production (ton/hour) | 132.6 | 70.6 | 97.7 |
| Benzene production (ton/hour) | 95.2 | 49.3 | 82.0 |
| Excess xylene mixture (ton/hour) | 0.0 | 7.0 | 22.6 |

TABLE 6-continued

|  | Example | Com. Example 1 | Com. Example 2 |
|---|---|---|---|
| Excess toluene (ton/hour) | 0.0 | 5.3 | 0.0 |
| Feed rate to Parex process (ton/hour) | 259.5 | 261.5 | 261.6 |
| Para-xylene concentration in the feed to Parex process | 24.6 wt % | 27.8 wt % | 23.6 wt % |

Reviewing the results shown in Table 6, the para-xylene concentration in the feed to the simulated moving bed para-xylene separation process in the Example according to the present invention was improved as compared to the Comparative example 2, and the amount of para-xylene and benzene produced from the process during the same period was increased by 34.9 tons/hour and 13.2 tons/hour, as compared to the Comparative example 2. When it is calculated as production in one year, it can be found that production increment of 306,000 tons and 116,000 tons may be obtained, respectively.

INDUSTRIAL APPLICABILITY

As it has been described so far, the separation method of aromatic compounds according to the present invention can make significant improvement in para-xylene and benzene production in the overall process, as compared to the conventional aromatic compound separation process.

The invention claimed is:

1. A method for separating aromatic compounds using a simulated moving bed adsorptive chromatography and a crystallization process, comprising:
   removing a non-aromatic compound from a mixture of aromatic compounds having 7 or less carbon atoms by a sulfolan process;
   fractionating benzene/toluene;
   fractionating an aromatic compound which separates aromatic compounds having 8 or more carbon atoms;
   selectively disproportionating toluene;
   transalkylating;
   crystallizing to separate para-xylene;
   separating para-xylene with a simulated moving bed; and
   isomerizing xylene;
   pretreating a xylene mixture with the simulated moving bed between the fractionating the aromatic compound step and the separating the para-xylene with the simulating moving bed step; and
   an additional isomerizing of xylene to which the xylene mixture from the simulated moving bed xylene mixture pretreating is inputted, wherein
   a resultant of the sulforan process is inputted to the fractionating of benzene/toluene step,
   the toluene from the fractionating of benzene/toluene is inputted to the selectively disproportionating of toluene step and the transalkylating step,
   some of the resultant of the selective disproportionating of toluene step is inputted again to the fractionating of benzene/toluene step,
   a residual amount of the resultant of the selective disproportionating of toluene step is inputted to an additional benzene/toluene fractionating step,
   the toluene separated from the additional benzene/toluene fractionating step is inputted to the selective disproportionating of toluene step again,
   a xylene mixture separated from the additional benezene/toluene fractionating is inputted to the crystallizing for para-xylene separation step,
   a residual xylene mixture other than the para-xylene is inputted to the simulated moving bed separating of para-xylene step,
   the xylene mixture from the fractionating the aromatic compound step is inputted to the simulated moving bed separating the para-xylene, and
   the xylene mixture from the simulated moving bed separating the para-xylene step is inputted to the isomerizing the xylene step.

2. The method for separating aromatic compounds according to claim 1, wherein the pre-treating the xylene mixture step and the additional isomerizing the xylene step comprise the following steps:
   (1) inputting a part of a xylene mixture that is to be inputted to the simulated moving bed separating the para-xylene step, to the simulated moving bed pre-treating the xylene mixture step;
   (2) inputting a xylene mixture containing 80% by weight or more para-xylene in the resulted product obtained from said simulated moving bed pre-treating the xylene mixture, to the crystallizing step for para-xylene separation, and the remaining portion of the xylene mixture is inputted to the additional isomerizing the xylene step;
   (3) re-inputting the resulted product obtained from the additional isomerizing the xylene step to the fractionating the aromatic compound step.

3. The method for separating aromatic compounds according to claim 2, wherein a part of the xylene mixture containing 80% by weight or more para-xylene to be inputted to the crystallizing step for para-xylene separation of the step (2), is inputted to the separating para-xylene with the simulated moving bed step.

4. The method for separating aromatic compounds according to claim 2, wherein a portion of the resulted products from the additional isomerizing of xylene step which are to be inputted to the fractionating of the aromatic compound of the step (3), is inputted to the fractionating of benzene/toluene step.

5. The method for separating aromatic compounds according to claim 1, wherein the toluene is additionally supplied to the selective disproportionating of toluene step.

6. The method for separating aromatic compounds according to claim 1, wherein the xylene mixture is additionally supplied to the fractionating of the aromatic compound step.

7. The method for separating aromatic compounds according to claim 2, wherein the toluene is additionally supplied to the selective disproportionating of toluene step.

8. The method for separating aromatic compounds according to claim 3, wherein the toluene is additionally supplied to the selective disproportionating of toluene step.

9. The method for separating aromatic compounds according to claim 4, wherein the toluene is additionally supplied to the selective disproportionating of toluene step.

10. The method for separating aromatic compounds according to claim 2, wherein the xylene mixture is additionally supplied to the fractionating of the aromatic compound step.

11. The method for separating aromatic compounds according to claim 3, wherein the xylene mixture is additionally supplied to the fractionating of the aromatic compound step.

12. The method for separating aromatic compounds according to claim 4, wherein the xylene mixture is additionally supplied to the fractionating of the aromatic compound step.

13. A method for separating aromatic compounds, comprising:
- inputting a resultant of a sulfolan process which is a non-aromatic compound removed from a mixture of aromatic compounds having 7 or less carbon atoms to a fractionating of benzene/toluene step;
- inputting toluene from the fractionating of benzene/toluene to a selective toluene disproportionating step and a transalkylating step;
- inputting at least one resultant of the selective toluene disproportionating step to the fractionating of benzene/toluene step;
- inputting a residual amount of the resultant of the selective disproportionating of toluene step to an additional step of fractionating benzene/toluene;
- inputting the toluene separated from the additional fractionating of benzene/toluene step to the selective disproportionating of toluene step;
- inputting a xylene mixture separated from the additional fractionating of benzene/toluene step to a crystallizing for para-xylene separation step;
- inputting a residual xylene mixture other than the para-xylene to a step of separating para-xylene with a simulated moving bed;
- inputting the xylene mixture from an aromatic compound fractionation to the step of separating para-xylene with the simulated moving bed, wherein
- the aromatic compound fractionation separates aromatic compounds having 8 or more carbon atoms;
- inputting the xylene mixture from the simulated moving bed para-xylene separating step to a xylene isomerizating step;
- the pretreating of the xylene mixture with the simulated moving bed being between the aromatic compound fractionating and the simulated moving bed para-xylene separating; and
- isomerizing an additional of the xylene mixture from the simulated moving bed xylene mixture pretreating.

14. The method for separating aromatic compounds according to claim 13, wherein the pre-treating the xylene mixture step and the additional isomerizing the xylene step comprises:
- (1) inputting a part of a xylene mixture that is to be inputted to the simulated moving bed para-xylene separating step, to the simulated moving bed xylene mixture pre-treating step;
- (2) inputting a xylene mixture containing 80% by weight or more para-xylene in the resulted product obtained from said simulated moving bed xylene mixture pre-treating step, to the crystallizing for para-xylene separation step, wherein,
- a remaining portion of the xylene mixture is inputted to the additional isomerizing of xylene step;
- (3) re-inputting the resulted product obtained from the additional xylene isomerizing step to the step of fractionating the aromatic compound.

15. The method for separating aromatic compounds according to claim 14, wherein a part of the xylene mixture containing 80% by weight or more para-xylene to be inputted to the crystallizing for para-xylene separation of the step (2), is inputted to the simulated moving bed separating step.

16. The method for separating aromatic compounds according to claim 14, wherein a portion of the resulting products from the additional xylene isomerizing step which are to be inputted to the aromatic compound fractionating of the step (3), is inputted to the fractionation of benzene/toluene step.

17. The method for separating aromatic compounds according to claim 13, wherein the toluene is additionally supplied to the step of selective disproportionating of toluene.

18. The method for separating aromatic compounds according to claim 13, wherein the xylene mixture is additionally supplied to the fractionating of the aromatic compound step.

* * * * *